(12) United States Patent
Stoyanova et al.

(10) Patent No.: US 10,112,877 B2
(45) Date of Patent: Oct. 30, 2018

(54) PROCESS FOR OLEFIN PRODUCTION BY METATHESIS AND REACTOR SYSTEM THEREFOR

(71) Applicant: Borealis AG, Vienna (AT)

(72) Inventors: Mariana Stoyanova, Berlin (DE); Evgeny Kondratenko, Rostock (DE); David Linke, Berlin (DE); Eberhard Ernst, Weissenfels (DE); Rene Dicke, Leonding (AT)

(73) Assignee: Borealis AG, Vienna (AT)

( * ) Notice: Subject to any disclaimer, the term of this patent is extended or adjusted under 35 U.S.C. 154(b) by 0 days.

(21) Appl. No.: 15/105,692

(22) PCT Filed: Dec. 19, 2014

(86) PCT No.: PCT/EP2014/078643
§ 371 (c)(1),
(2) Date: Jun. 17, 2016

(87) PCT Pub. No.: WO2015/091905
PCT Pub. Date: Jun. 25, 2015

(65) Prior Publication Data
US 2016/0318830 A1    Nov. 3, 2016

(30) Foreign Application Priority Data
Dec. 20, 2013 (EP) .................................. 13198981

(51) Int. Cl.
*C07C 6/04* (2006.01)
*C07C 6/02* (2006.01)
(Continued)

(52) U.S. Cl.
CPC .............. *C07C 6/04* (2013.01); *B01J 8/0457* (2013.01); *C07C 7/1485* (2013.01);
(Continued)

(58) Field of Classification Search
CPC ..... C07C 6/02; C07C 6/04; C07C 5/25; C07C 7/12
(Continued)

(56) References Cited

U.S. PATENT DOCUMENTS 3,365,513 A    1/1968    Heckelsberg
3,865,751 A    2/1975    Banks et al.
(Continued)

FOREIGN PATENT DOCUMENTS

CA        925885 A      5/1973
CN     102188965 A      9/2011
(Continued)

OTHER PUBLICATIONS

Banks et al., "New Developments and Concepts in Enhancing Activities of Heterogenous Metathesis Catalysts", Journal of Molecular Catalysis, 1985, vol. 28:1-3, pp. 117-131.
(Continued)

*Primary Examiner* — Thuan D Dang
(74) *Attorney, Agent, or Firm* — The Webb Law Firm (57) ABSTRACT

A process for obtaining an olefin by metathesis including at least two reaction pathways. In at least one first reaction pathway at least one stream with at least one olefin as starting material is fed to at least one first pre-bed reactor with at least one pre-bed having at least one compound selected from the group of alkaline earth metal oxides. The stream leaving the at least one first pre-bed reactor is subsequently fed to at least one main catalyst bed reactor downstream of the at least one first pre-bed reactor including at least one main catalyst bed with at least one first catalyst component comprising a metathesis catalyst, and at least one second catalyst component comprising a catalyst for double bond isomerization, whereby the first and second catalyst are physically mixed with each other.

15 Claims, 2 Drawing Sheets

(51) Int. Cl.
  *C07C 5/25* (2006.01)
  *C07C 7/12* (2006.01)
  *B01J 8/04* (2006.01)
  *C07C 7/148* (2006.01)

(52) U.S. Cl.
  CPC .. *B01J 2208/025* (2013.01); *B01J 2219/0004* (2013.01); *B01J 2219/00038* (2013.01); *C07C 2521/08* (2013.01); *C07C 2523/02* (2013.01); *C07C 2523/30* (2013.01)

(58) Field of Classification Search
  USPC .................. 585/643, 646, 664, 670, 823
  See application file for complete search history.

(56) References Cited

U.S. PATENT DOCUMENTS

| | | |
|---|---|---|
| 3,915,897 A | 10/1975 | Reusser et al. |
| 4,071,471 A | 1/1978 | Banks et al. |
| 4,547,617 A | 10/1985 | Welch |
| 4,575,575 A | 3/1986 | Drake et al. |
| 5,489,726 A * | 2/1996 | Huss, Jr. ............ B01J 8/0242 585/671 |
| 6,271,402 B1 | 8/2001 | Singh et al. |
| 7,525,007 B2 | 4/2009 | Sumner |
| 7,977,522 B2 | 7/2011 | Takai et al. |
| 9,040,764 B2 | 5/2015 | Ramachandran et al. |
| 2003/0024855 A1 | 2/2003 | Mesher |
| 2006/0183627 A1 | 8/2006 | Stephan et al. |
| 2007/0225527 A1 | 9/2007 | Wuerkert et al. |
| 2010/0056839 A1 | 3/2010 | Ramachandran et al. |
| 2010/0167911 A1 | 7/2010 | Shum |
| 2012/0016172 A1 | 1/2012 | Miyazoe et al. |

FOREIGN PATENT DOCUMENTS

| | | |
|---|---|---|
| EP | 1854776 A1 | 11/2007 |
| KR | 2002078840 A * | 10/2002 |
| WO | 2005049534 A1 | 6/2005 |
| WO | 2010113993 A1 | 7/2010 |
| WO | 2011011173 A2 | 1/2011 |

OTHER PUBLICATIONS

Wang et al., "Effect of support nature on WO3/SiO2 structure and butene-1 a metathesis," Applied Catalysis A: General 250, 2003, pp. 25-37.

* cited by examiner

PROCESS FOR OLEFIN PRODUCTION BY METATHESIS AND REACTOR SYSTEM THEREFOR

CROSS-REFERENCE TO RELATED APPLICATIONS

This application is the United States national phase of International Application No. PCT/EP2014/078643 filed Dec. 19, 2014, and claims priority to European Patent Application No. 13198981.6 filed Dec. 20, 2013, the disclosures of which are hereby incorporated in their entirety by reference.

BACKGROUND OF THE INVENTION

Field of the Invention

The present invention relates to a process for olefin production by metathesis and a reactor system for conducting said process.

Description of Related Art

Butenes are the $C_4H_8$ mono-olefin isomers such as 1-butene, cis-2-butene, trans-2-butene and iso-butene (2-methylpropene). If it is not specifically mentioned, cis-2-butene, trans-2-butene are also called as 2-butene within the frame of the present invention. The sum of cis-2-butene, trans-2-butene, and 1-butene is denoted as n-butenes. Butenes are almost always commercially produced as by-products in a petroleum refinery by cracking processes or by catalytic ethene dimerisation. Butenes can be used for multiple purposes like in the manufacture of polymers and other chemicals like insecticides, antioxidants, adhesives, sealants or elastomers.

The use of n-butenes for the production of propene has gained industrial importance in the last decades. The synthesis of propene using n-butenes as starting material is based on the metathesis reaction. Hereby, 2-butene is converted in the presence of ethene to propene according to the following overall reaction scheme:

ethene+2-butene $\rightleftharpoons$ 2 propene

This reaction occurs typically in the presence of a catalyst comprising metal oxide of the group 6 or 7 of the periodic system of the elements (PSE). Typical active components of catalysts used for olefin metathesis are tungsten oxide supported on silica (U.S. Pat. No. 3,365,513) or rhenium oxides and molybdenum oxides supported on alumina or silica alumina (U.S. Pat. No. 4,547,617; U.S. Pat. No. 6,281,402).

Various modifications and improvements of the metathesis catalysts have been described. The physical mixing of the metathesis catalyst with an isomerisation catalyst for shifting the double bond in 1-butene to 2-butene has been proven to increase the overall production yield (U.S. Pat. No. 3,865,751; U.S. Pat. No. 3,915,897; U.S. Pat. No. 4,575,575). Typical double bond isomerisation catalysts include basic metal oxides as for instance magnesium oxide or calcium oxide. The use of magnesium oxide (MgO) as a co-catalyst enables reduction of the reaction temperature to 250-300° C. from approximately 400° C. for pure silica supported tungsten oxide ($WO_3/SiO_2$). The weight ratio of MgO to $WO_3/SiO_2$ is in the range of 0.1-20. Magnesium oxide has the function to isomerise 1-butene to 2-butene since both olefins are present in technical feeds. It is important to highlight that magnesium oxide alone shows negligible metathesis activity.

Besides its ability to act as an isomerisation catalyst magnesium oxide has also been known for its ability to remove or destroy traces of contaminants from the olefin feed that are detrimental to metathesis catalysts, in particular when used as a "guard bed" (J. Mol. Cat. 1985, 28:117-131). Magnesium oxide can be for instance arranged on top of a composition comprising the metathesis catalyst and an isomerisation catalyst (US 2010/0056839 A1, US 2010/167911 A1). Here the optimal catalyst activation is combined with the guard pre-bed function to remove poisons and the isomerisation of 1-butene to 2-butene. When applying this approach a technical metathesis reactor is typically filled with a mixture of MgO and $WO_3/SiO_2$ as main bed and an MgO pre-bed upstream of the main bed.

However, the known technical metathesis catalysts for propene production suffer from a decrease in their activity due to coke formation. The largest amount of coke during the propene production cycles is formed on the magnesium oxide surface. Moreover, the coke concentration on the surface is growing over the whole time on stream in increasing amounts. The coke amount deposited on the silica supported tungsten oxide reaches very fast a steady state value, which is lower than on MgO. In a metathesis cycle, propylene production starts to decrease when active isomerisation sites on the surface of MgO located as a pre-bed upstream of the main catalysts bed (mixture of MgO and $WO_x/SiO_2$) are completely covered with coke.

Therefore, a regeneration of the catalyst is imperative if the catalytic activity decreases below a certain level during the production cycle. One regeneration method is described for instance in US 2010/0167911 A1. Here a used catalyst mixture is regenerated in the presence of an oxygen containing gas followed by contacting the decoked catalyst mixture with steam at a temperature in the range of 100 to 300° C.

The decoking step is usually performed at temperatures between 450° C. to 800° C. Such high-temperature treatment additionally diminishes the lifetime both of the metathesis catalyst and in particular the isomerisation catalyst.

In WO 2011/011173 A1 it is reported that the performance of MgO as isomerisation catalyst after several regeneration/reaction cycles is low. The reduced performance of the catalyst may lead to a rapid build-up of 1-butene in the system over time thus limiting the overall reactor performance. It is thought that the loss of activity as a result of multiple cycles of regeneration is due to the loss of surface area of the catalyst particle due to sintering created by the higher temperatures required for coke removal. The loss of surface area results in loss of MgO activity for isomerisation and as adsorbent for poisons.

The on-purpose production of propene is the main target of the commercial metathesis technology. It is of general interest to reduce the catalyst costs and to improve in this way the process economy. The catalyst costs are determined to a large extent by the life time of the catalyst. The catalyst performance deteriorates typically after 12 to 15 metathesis/regeneration cycles. The high regeneration temperatures have an influence on the available active surface of MgO and change the distribution of supported $WO_x$ species and in this way the number of active sites (Wang et al., Applied Catalysis A: General 250, 2003, 25-37). Normally the whole reactor filling must be replaced when the end of the catalyst life time is reached. This requires an interruption of the production process.

It is therefore highly desirable to provide a process which allows for an optimisation of the metathesis process by improving the overall yield and by reducing costs through prolonged catalyst life time.

SUMMARY OF THE INVENTION

Accordingly, a process for obtaining an olefin by metathesis is provided which comprises at least two reaction pathways.

In at least one first reaction pathway at least one stream comprising at least one olefin as starting material is fed to at least one first pre-bed reactor with at least one pre-bed comprising at least one compound selected from the group of alkaline earth metal oxides, and the stream leaving the at least one first pre-bed reactor is subsequently fed to at least one main catalyst bed reactor arranged downstream of the at least one first pre-bed reactor wherein said main catalyst bed reactor comprises at least one main catalyst bed comprising at least one first catalyst component comprising a metathesis catalyst, and at least one second catalyst component comprising a catalyst for double bond isomerisation, whereby the first and second catalyst are physically mixed with each other.

In at least one second reaction pathway the at least one stream comprising at least one olefin as starting material is re-directed from the at least one first pre-bed reactor to at least one second pre-bed reactor with at least one pre-bed comprising at least one compound selected from the group of alkaline earth metal oxides, and the stream leaving the at least one second pre-bed reactor is subsequently fed to the at least one main catalyst bed reactor arranged downstream of the at least one second pre-bed reactor.

Thereby, the operational temperature $T_{10}$ of the first pre-bed reactor and the operational temperature $T_{20}$ of the second pre-bed reactor is in each case lower than the operational temperature $T_{30}$ of the main catalyst bed reactor.

The present method is thus conducted in a reactor system comprising at least one first pre-bed reactor with at least one pre-bed, at least one second pre-bed reactor with at least one pre-bed and at least one main catalyst bed reactor with the main catalyst bed arranged downstream of the first pre-bed reactor and the second pre-bed reactor.

In the first reaction pathway the olefin is fed to the first pre-bed reactor with the first pre-bed, for instance consisting of MgO, wherein isomerisation of the olefin such as n-butene is effected and simultaneously traces of contaminants from the olefin feed are removed or destroyed.

The olefin stream leaving the first pre-bed reactor is subsequently fed into the main metathesis reactor comprising the main catalyst bed of isomerisation catalyst and metathesis catalyst.

As described previously both the pre-bed as well as the main catalyst bed are prone to deactivation in the course of the metathesis due to coking. The coking effects in particular the pre-bed.

If the metathesis reaction is now slowing down as a result of the coking, for instance after a period of about 50-60 hours on stream, according to the present process the first pre-bed reactor is turned off and the olefin stream used as starting material is re-directed or switched to the second pre-bed reactor in the second reaction pathway. The effluent leaving the second pre-bed reactor (after isomerisation and removal of poison) is subsequently fed to the main catalyst bed reactor (metathesis synthesis reactor) for the actual metathesis reaction.

While the first pre-bed reactor is turned off said first pre-bed reactor or more precise the first pre-bed arranged in the first pre-bed reactor is subjected to a regeneration cycle. Thus, in an embodiment of the present process the at least one first pre-bed reactor is turned off during the second reaction pathway and is subjected to at least one regeneration cycle during turn-off.

The present process allows for a thermal regeneration solely of the pre-bed (and not the main catalyst bed). By doing so the thermal exposure (thermal load) of the main catalyst bed is reduced and the life time of the main catalyst bed is extended. Furthermore, there is no need to replace the whole reactor content if the end of catalyst life time is reached which is determined by the life time of the pre-bed material such as MgO. In this way the overall costs of the catalyst and therefore of the metathesis process are reduced. Furthermore, the length of the propene production cycle of the main-bed reactor between two regeneration steps is extended and thus longer production cycles are realized. This increases the life time of the catalyst and the costs per time unit decrease.

The examples provided below clearly demonstrate that time on stream (production cycle length) of the main-bed reactor by using the present process is significantly longer compared to the conventional process, i.e. one reactor both for MgO pre-bed and main catalyst bed. If the pre-bed magnesium oxide is damaged due to the high regeneration temperatures, only 25% (in case of one pre-reactor) or 50% (in case of two pre-reactors) of the total catalyst amount has to be replaced.

In a further embodiment of the present process the number of reaction pathways can be more than two. The number of reaction pathways and thus number of switching between the pre-bed reactors depends strongly on the quality of the main catalyst and the purity of the olefin feed. For example, the number of reaction pathways can be up to 3 or even larger. This means that if the olefin production decreases or slows down using the second pre-bed reactor said second pre-bed reactor is subsequently turned off and the olefin stream with the starting material is re-directed or switched again to the first pre-bed reactor after regeneration of the first pre-bed reactor; a third reaction pathway of olefin metathesis is then started using the first regenerated pre-bed reactor again. When turned off the second pre-bed reactor is then subjected to at least one regeneration cycle. After regeneration of the second pre-bed reactor the olefin feed can be re-directed again to the now regenerated second pre-bed reactor and a fourth metathesis reaction pathway is started. In general, this process of turning-off a pre-bed reactor, re-directing the olefin feed to another pre-bed reactor, regenerating the turned off pre-bed reactor and re-using the regenerated pre-bed reactor can be repeated as often as possible or as long as the synthesis rate or product yield is in a reasonable range such that the process is still economical.

It is preferred if in the present process the time on stream for one reaction pathway can be larger than 40 h, preferably larger than 50 h, most preferably larger than 60 h. It is conceivable that the time on stream for one reaction pathway is up to 70 or 80 h or even above. The time on stream may however decrease with growing pathways numbers. For example in a third pathway the time on stream may be larger than 20, preferably larger than 30 hours, most preferably larger than 30 hours. Again this time on stream for a reaction pathway depends on the quality of the main catalyst, such as the degree of aging, and the purity of the olefin feed.

In a further embodiment of the present process the mass ratio of the pre-bed in the first pre-bed reactor and the second pre-bed reactor to the main catalyst bed in the main catalyst bed reactor is between 1:5 and 2.5:1, preferably between 1:4 and 1:1, most preferably between 1:3 and 1:2. For example the mass ratio of pre-bed to main catalyst bed may be 1:4.8, 1:4, 1:2.5 or 1:1.2. In the present process an excess of the main catalyst bed in respect to the pre-bed is preferred.

In a further embodiment of the present process the operational temperatures $T_{10}$, $T_{20}$ of each of the pre-bed reactors is the same or lower than the operational temperature $T_{30}$ of the main catalyst bed reactor.

In a preferred embodiment of the present process the operational temperature $T_{10}$ of the first pre-bed reactor, the operational temperature $T_{20}$ of the second pre-bed reactor and the operational temperature $T_{30}$ of the main catalyst bed reactor in each case is in a range between 150° C. and 350° C., preferably 200° C. and 340° C., preferably 260° C. and 330° C., preferably 270° C. and 310° C., preferably 280° C. and 300° C., mostly preferably at 300° C., wherein the operational temperatures of the pre-bed reactors are lower than the operational temperature in the main catalyst bed.

In an embodiment, the operational temperature of the first pre-bed reactor and the operational temperature of the second pre-bed reactor are in a range of 150° C. to 350° C. The pre-bed operated at such temperatures mainly serves for isomerizing the olefin feed, in particular the n-butene feed, which contains trans-olefins (such as trans-butene) and cis-olefins (such as cis-butene), to obtain the desired cis-olefin (such as cis-butene) which is the most suited (or factual) starting material for the metathesis reaction to be performed. The isomerization reaction in the pre-bed is achieved due to using a temperature of 150° C. to 350° C. This temperature range is significantly higher than the temperature in pre-treatment steps disclosed in prior art. Rather, the pre-treatment disclosed in prior art mainly serves for feed purification.

If the n-olefin mixture (such as an n-butene mixture) would directly be introduced into the main bed then much coking would occur there (as a by-product of the isomerization taking then place in the main bed) which of course would drastically decrease the life time of the main bed catalyst. In forcing the isomerization to take place in the pre-bed and switching the pre-beds according to the instantly claimed process, the coking products can be eliminated during regeneration of the pre-beds, while the life time of the main catalyst bed is significantly increased.

Moreover, when directly entering the n-olefin (such as n-butene) feed to the main bed without preceding isomerization, the product yield (such as propylene yield) would be lower because the coke formation is higher due to often higher temperatures in the main bed. If coke is formed, the respective substance cannot be used anymore as isomerized starting material.

In an embodiment the operational temperature $T_{10}$ of the first pre-bed reactor and the operational temperature $T_{20}$ of the second pre-reactor is at least 20° C., preferably at least 40° C., most preferably at least 50° C., outmost preferably at least 100° C. lower than the operational temperature $T_{30}$ of the main catalyst bed reactor. In an embodiment, the operational temperature $T_{10}$ of the first pre-bed reactor and the operational temperature $T_{20}$ of the second pre-bed reactor can be in each case in a range between 150° C. and 300° C., preferably 170° C. and 230° C., preferably 190° C. and 210° C., preferably 200° C. and 290° C., preferably 250° C. and 280° C., most preferably between 220° C. and 270° C., outmost preferably between 240° C. and 260° C., in particular at 250° C., and the operational temperature $T_{30}$ of the main catalyst bed reactor is preferably in a range between 250° C. and 350° C., preferably between 270° C. and 330° C., most preferably between 290° C. and 310° C., mostly preferred at 300° C.

As mentioned above, the pre-bed of the first pre-bed reactor and the second pre-bed reactor may undergo at least one regeneration cycle when turned off. Such a regeneration cycle of the pre-bed of the first pre-bed reactor and the second pre-bed reactor may comprise in each case a thermal treatment in an oxygen gas atmosphere at temperatures between 400° C. and 600° C., preferably between 420° C. and 550° C.

In a preferred embodiment the pre-bed is heated at 420° C. in an oxidizing atmosphere with 1-2 vol % oxygen, e.g. 1 vol % oxygen in nitrogen, followed by increasing the oxygen concentration to 3 to 4 vol %, preferably 3 vol % with a simultaneous temperature rise to 480° C. and a further increase of oxygen concentration to 5 to 7 vol % oxygen, preferably 6 vol % oxygen, with a simultaneous temperature rise to 525° C. Subsequently, the catalyst bed configuration is subjected to an air atmosphere at temperatures between 450° C. and 550° C., preferably 525° C., for 1 to 5 h, preferably 3 h, followed by cooling down to a temperature between 300° C. and 400° C., preferably to 400° C., in an inert gas atmosphere, such as nitrogen atmosphere.

It is to be understood that parameters provided above for regeneration and also further below for activation such as the heating and/or cooling times depend on the overall size of the pre-bed and the catalyst bed and the reactor size. In particular said heating and/or cooling times have to be adapted, accordingly. For instance, in case of an upscaling of the reactor size reduced heating rates may be practically in order to ensure a homogenous temperature increase throughout the catalyst bed.

In a further embodiment the metathesis catalyst of the main catalyst bed comprises metal oxides from metals of group 6 and 7 of the PSE, in particular tungsten oxide, molybdenum oxide and/or a precursor thereof, which are the active components and are deposited on at least one inorganic carrier. The most preferred metal oxide is tungsten oxide.

Preferably, the at least one inorganic carrier is selected from a group comprising silica, alumina, silica-alumina or aluminium phosphate. The inorganic carrier can contain at least about 0.1 wt % and up to 40 wt % of the active components. Amounts between 1 to 30 wt % are preferred, whereby amounts between 2 to 15 wt % are mostly preferred.

The metathesis catalyst may further comprise at least one oxide of a metal of group I of the PSE or a precursor thereof as for instance comprising oxides, hydroxides, carbonates, bicarbonates, nitrates, acetates of sodium or potassium or mixtures thereof. Especially preferred are the hydroxides of sodium and potassium. Said compounds have the function to modify the surface acidity of the silica in the metathesis catalyst. It is known that the bulk concentration of e.g. sodium in silica has to be lower than 500 ppm (WO 2005/049534). The amount of these modifying compounds can be between 0.01 and 10 wt %, preferably between 0.1 and 1.0 wt % with respect to the metathesis catalyst.

It is further possible that the metathesis catalyst undergoes a pre-treatment with at least one oxide of a metal of group 1 of the PSE or a precursor thereof. For example it is preferred if silica supported tungsten oxide is used as metathesis catalyst it undergoes a pre-treatment with potassium hydroxide.

The BET surface area of the metathesis catalyst is at least >10 m²/g, preferably at least >50 m²/g and mostly preferably at least >100 m²/g.

The particle size of the metathesis catalyst depends on the reactor size. When applied as powder like for instance in lab size reactors, the typical particle size of the metathesis catalyst is between 0.3-0.7 mm. When used in larger reactors like for instance technical reactors the particle size is in the range between 1 and 10 mm, preferably between 1 and 8 mm, most preferably between 1 and 5 mm.

In another preferred embodiment said second catalyst component for double bound isomerisation of the main bed composition comprises group 2 metal oxides, in particular magnesium oxide, calcium oxide, barium oxide or strontium oxide.

The main catalyst bed can then be prepared by admixture of the isomerisation catalyst and the metathesis catalyst. The catalysts are preferably mixed in form of powders, pellets or extrudates.

The amount of the isomerisation catalyst is preferably in excess of the amount of the metathesis catalyst. However, the isomerisation catalyst can also be used in lower amounts. In an embodiment the main catalyst bed comprises the at least one isomerisation catalyst component and the at least one metathesis catalyst component in a ratio between 5:1 and 1:1, preferably in a ratio 4:1 and 2:1, most preferably in a ratio of 3:1.

In a preferred embodiment of the present process the pre-bed of the first and second pre-bed reactors comprises in each case an oxide selected from the group consisting of magnesium oxide, calcium oxide, strontium oxide, barium oxide or mixtures thereof, in particular magnesium oxide. The pre-bed compound may be the same or different to the isomerisation catalyst used in the main catalyst bed. It is however preferred that magnesium oxide is used as pre-bed compound and as isomerisation catalyst in the main catalyst bed.

In another variant of the present process the compound used as pre-bed and/or the isomerisation catalyst in the main bed can undergo a thermal pre-treatment before use, wherein the pre-treatment comprises at least one cycle of successive treatment in an oxidizing and reducing atmosphere. For example, the pre-treatment cycle may comprise the steps of: a) heating the compound in an inert gas atmosphere to a temperature between 300° C. and 500° C., preferably 400° C.; b) treating the compound in an oxygen containing atmosphere at temperatures between 400° C. and 600° C., preferably between 500° C. and 550° C., most preferably at 525° C.; c) treating the compound in a hydrogen containing atmosphere at temperatures between 300° C. and 500° C., preferably at 400° C.; d) flushing the compound with an inert gas at temperatures between 400° C. and 600° C., preferably between 400° C. and 550° C., most preferably at 550° C.; and e) subsequent cooling down the compound, preferably to a temperature between 200 and 350° C., most preferably to 300° C.

Thus, in a further embodiment of the present process a pre-aged isomerisation catalyst such as pre-aged MgO can be used in the main catalyst bed as isomerisation catalyst while a pre-aged alkaline earth oxide e.g. pre-aged or pre-treated MgO is used simultaneously as pre-bed. The isomerisation catalyst of the main catalyst bed and the alkaline earth oxide of the pre-bed were preferably pre-treated in the same manner and under the same conditions as described above.

In another embodiment of the present process the catalyst bed of main catalyst bed comprising metathesis catalyst and isomerisation catalyst in the main catalyst bed reactor and the pre-bed in each of the first and second pre-bed reactors are activated before the actual metathesis reaction of olefins.

Such an activation process may comprises the steps of:
a) heating the main catalyst bed and/or pre-bed in an inert gas atmosphere to a temperature between 300° C. and 500° C., preferably 400° C.;
b) treating the main catalyst bed and/or pre-bed in an oxygen containing atmosphere e.g. such as air at temperatures between 400° C. and 600° C., preferably 400° C. and 550° C.;
c) treating the main catalyst bed and/or pre-bed in a hydrogen containing atmosphere at temperatures between 300° C. and 500° C., preferably at 400° C.,
d) heating the main catalyst bed and/or pre-bed in an inert gas atmosphere at temperatures between 400° C. and 600° C., preferably 400° C. and 550° C.; and
e) subsequent cooling down the main catalyst bed and/or pre-bed in an inert gas atmosphere.

In a typical embodiment of the activation procedure the main catalyst bed and/or pre-bed is heated starting at room temperature for example at a heating rate of 5 K/min until an end temperature e.g. of about 400° C. is reached and is held at this temperature for about 2 hours.

In the next step the main catalyst bed and/or pre-bed is treated in air, wherein the start temperature may be 400° C. and the end temperature may be 525° C. The heating rate is for example about 5 K/min during the oxidation. The holding time at the end temperature may be about 2 hours.

Subsequently the main catalyst bed and/or pre-bed treated in the oxidizing atmosphere is cooled down in an inert gas atmosphere, such as nitrogen gas atmosphere from the oxidation temperature of e.g. 525° C. to 400° C. (for example with a of cooling rate 2 K/min) and is held at the latter temperature for about 0.5 h. The treatment of the main catalyst bed and/or eventually of the pre-bed under reducing conditions is carried out in a gas mixture of nitrogen and hydrogen with a molar ratio of about 80:20, preferably 70:30 at e.g. about 400° C. for about 0.5-1 h, preferably for about 0.5 h. Following the reduction the catalyst is now purged with nitrogen at 400° C. for about 0.5-1 h, preferably for about 0.5 h.

The main catalyst bed and/or pre-bed treatment under reducing conditions is followed by a heating (desorption) step in an inert gas atmosphere, e.g. nitrogen gas. The desorption step may last 10-20 h, preferably 14-16 h. During this time the temperature may be raised from about 400° C. to about 550° C. for example with a heating rate of about 5 K/min. Finally, the main catalyst bed and/or pre-bed is cooled down in an inert gas atmosphere, e.g. nitrogen gas.

The metathesis reaction is preferably performed at a weight hourly space velocity (WHSV) in the range between 1 and 100 $h^{-1}$, preferably between 1 and 50 $h^{-1}$, more preferably between 1 and 10 $h^{-1}$ (the WHSV values are referring to the main catalyst bed and the fed 2-buten).

In an embodiment the one of the at least two olefins used as starting material comprises at least two carbon atoms, such as ethene, and the second of the at least two olefins used as starting material comprises at least four carbon atoms, such as 2-butene. The mole ratio between said olefin comprising at least two carbon atoms and the olefin comprising at least four carbon atoms can be between 1 and 20, preferably 1 and 10, mostly preferably between 1 and 5.

The at least two olefins may be supplied to the first pre-bed reactor or second pre-bed reactor as a mixed stream or in form of separated streams. When using 2-butene as starting material, the butene component may be supplied as cis- or trans-2-butene or mixtures thereof. A technical 2-butene stream may contain additional small amounts of n-butane, isobutane, isobutene, 1-butene. In some embodiments the mixed C4 stream is pre-treated to increase the 2-butene content in the feed for the metathesis reaction. If a crude C4 cut from an e.g. naphtha cracker is used compounds like 1,3-butadiene, allene or acetylenes have to be removed by a selective hydrogenation step.

The olefin mixture is then contacted with the pre-bed in the first or second pre-bed reactor, whereby a partial isomerisation of 1-butene to 2-butene may occur. When entering the main catalyst bed in the main catalyst bed reactor comprising the metathesis catalyst and the isomerisation catalyst, isomerisation in particular of 1-butene to 2-butene and the synthesis of propene from ethene and 2-butene occur. Besides propene also other reaction products can be formed such as for example C5-C6 olefins.

The process may be carried out by contacting the olefins with the catalysts in the liquid phase or the gas phase depending on structure and molecular weight of the olefins used as starting material, the catalyst used and/or the reaction conditions applied such as pressure, temperatures etc. Diluents such as saturated aliphatic hydrocarbons, such as methane, ethane, propane, butane and/or inert gases like nitrogen or argon might be suitable. In any case, the presence of deactivating substances like water or oxygen should be avoided.

The metathesis catalyst is very sensitive to impurities in the feed stream. Such feed poisons are, for example, strong polar or protic compounds such as N-, O-, S- and halogen comprising compounds or carbon oxide derivatives. Typical examples are water, alcohols, ethers, ketones, aldehydes, acids, carbon dioxide, carbon monoxide, carbon oxide sulfide and the like. The consequences are reduced catalyst activity and shortened cycle times. Therefore the feed stream must be purified by passing it through suitable adsorbents before feeding to the reactor.

It is in general also possible to conduct the reaction in the presence of hydrogen (EP 1854776 A1).

The effluent from the main catalyst bed (metathesis) reactor can be sent to a separation system for separating the product(s) from unreacted feed components. For instance, the products of the separation system may include ethene, propene, C4- and C5-compounds. The propene separated from the reaction stream is characterised by a high purity. The ethene and C4 olefins may be recycled back to the metathesis reactor or to a pre-treatment stage.

The present process is conducted in a reactor system comprising
  at least one first pre-bed reactor with at least one pre-bed comprising at least one compound selected from the group of alkaline earth metal oxides,
  at least one second pre-bed reactor with at least one pre-bed comprising at least one compound selected from the group of alkaline earth metal oxides, and
  at least one main catalyst bed reactor comprising at least one main catalyst bed comprising at least one first catalyst component comprising a metathesis catalyst, and at least one second catalyst component comprising a catalyst for double bond isomerisation, whereby the first and second catalyst are physically mixed with each other,
  wherein the at least one main catalyst bed reactor is arranged downstream of the at least one first pre-bed reactor and the at least one second pre-bed reactor, respectively.

The compounds used in the reactor system are identical to the ones previously described in context of the process. Thus, it is referred to the above description.

In another embodiment of the present reactor system the at least two pre-bed reactors are arranged in parallel to each other.

The first and second pre-bed reactors and the main catalyst bed reactor are preferably fixed-bed reactors. Basic types of catalytic fixed-bed reactors are the adiabatic fixed-bed reactor and the isothermal fixed-bed reactor. The adiabatic fixed-bed reactor is preferred for technical processes. Pre-bed and main-bed are usually provided in the fixed-bed reactor in form of random packings of powders, pellets or extrudates, for instance of catalytic pellets.

It is furthermore preferred if the at least two pre-bed reactors and the at least one main catalyst bed reactor have in each case a length to diameter ratio (l/d ratio) between 1 and 15, preferably between 1 and 10, most preferably between 1 and 5, even more preferably between 1.5 and 3.5.

However, it is also conceivable and possible that the first and/or second pre-bed reactor and the main catalyst bed reactor are of different volumes. It is for instance of an advantage if the first and/or second pre-bed reactor is of a smaller volume than the main catalyst bed reactor. The volume ratio (V/V) of pre-bed reactors and main catalyst reactor may be 0.05-1.0, preferably 0.1-0.8, more preferably 0.2-0.5, most preferably 0.2-0.3.

In general the reactor construction and dimension of the reactors are determined by different process factors: the minimum diameter of the reactor should be at least 10 times larger than the particle diameter of the catalyst, the height of the catalyst bed should be at least 50 times larger than the particle diameter, the bulk density of the pre-bed and main bed components are of importance as well as the desired Weight Hourly Space Velocity.

The first and/or second pre-bed reactors are connected to the main catalyst bed reactor by a suitable pipeline for transferring the olefin stream leaving the first or second pre-bed reactor into the main catalyst bed reactor where the actual metathesis reaction takes place. The connecting pipeline should be as short as possible for avoiding any undesired side reactions. It is preferred if the connecting pipeline is temperature controlled and equipped with a trace heating. The temperature of the connecting pipeline is preferably in the same range as the operational temperature $T_{30}$ of the main catalyst bed reactor. For instance the olefin stream leaving the first or second pre-bed reactor may be heated in said pipeline to a temperature of about 300° C.

BRIEF DESCRIPTION OF THE DRAWINGS

The present invention is further explained in more detail by the means of the following examples with reference to the Figure. It shows.

DETAILED DESCRIPTION OF THE INVENTION

Figure 1:
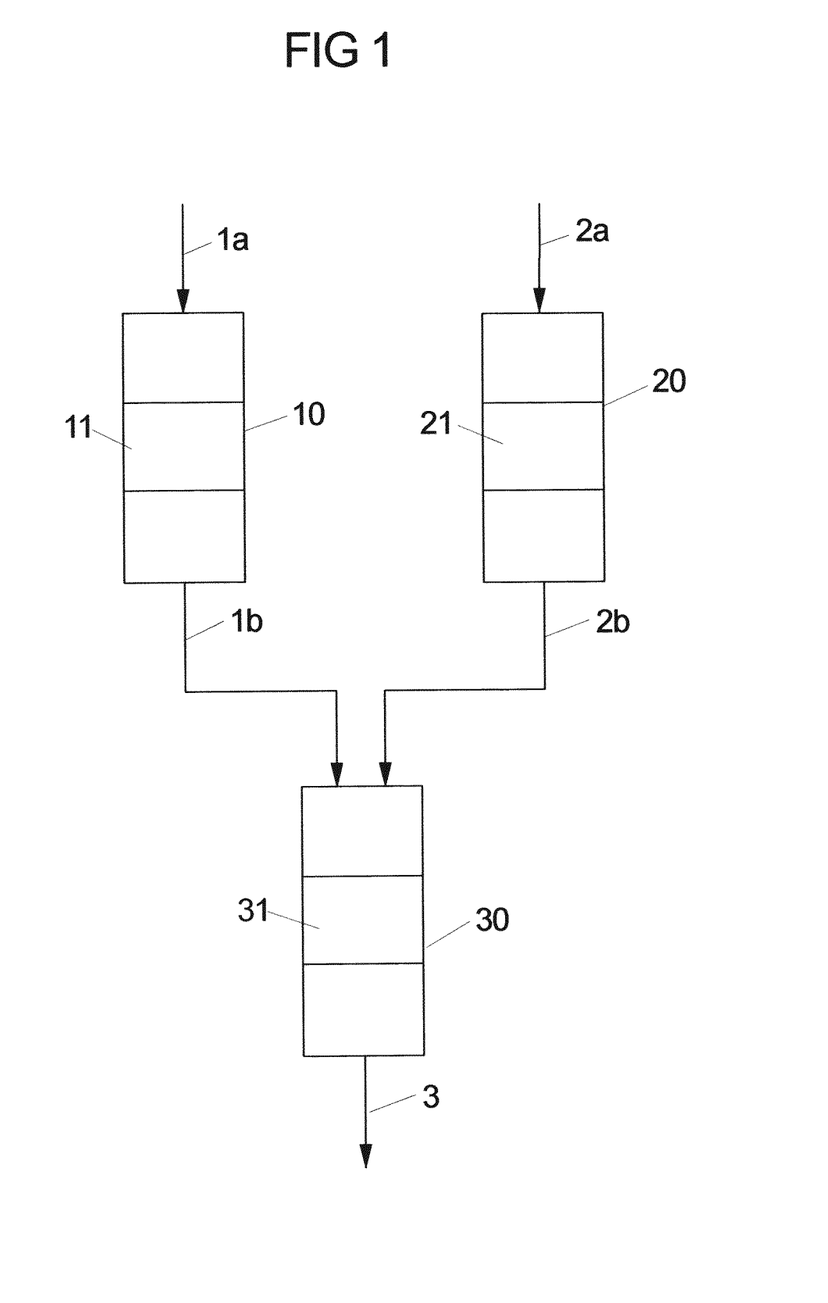
FIG. 1 an embodiment of the reactor system according to the invention.

FIG. 1 refers to a reactor system for conducting the present process comprising a first pre-bed reactor (10) with at least one pre-bed (11) made of magnesium oxide (0.3-0.7 mm) and a second pre-bed reactor (20) with at least one pre-bed (21) made of magnesium oxide (0.3-0.7 mm) as well. First and second pre-reactor (10, 20) are arranged parallel to each other.

The main catalyst bed reactor (30) comprising the main catalyst bed (31) being a physical mixture of MgO (0.3-0.7 mm) and WOx/SiO$_2$ (0.3-0.7 mm) with a mass ratio of 3:1 is arranged downstream of the at least one first pre-bed reactor (10) or the at least one second pre-bed reactor (20), respectively.

In the first reaction pathway the olefin mixture (1a) of ethene and n-butene is now fed to the first pre-bed reactor (10), wherein isomerisation of the olefin such as n-butene is effected and simultaneously traces of contaminants from the olefin feed are removed or destroyed.

The olefin stream (2a) leaving the first pre-bed reactor (10) is subsequently fed into the main metathesis reactor (30) where metathesis takes place. The product stream (3) leaving the main metathesis reactor (30) consists of propene and traces of non-reacted starting material.

If the metathesis reaction in the metathesis reactor (30) is now slowing down as a result of the coking process, for instance after a period of about 50-60 hours on stream, the first pre-bed reactor (10) is turned off and the olefin stream of ethene and n-butene (1b) is re-directed or switched to the second pre-bed reactor (20) in the second pathway step.

The effluent (2b) leaving the second pre-bed reactor (20) after isomerisation and removal of poison is subsequently fed to the main metathesis reactor (30) for the actual metathesis reaction.

While the first pre-bed reactor (10) is turned off said first pre-bed reactor is subjected to a regeneration cycle.

If now the olefin production decreases or slows down using the second pre-bed reactor (20) for instance after a time on stream of about 50 hours said second pre-bed reactor (20) is subsequently turned off and the olefin stream with the starting material is re-directed or switched again to the first pre-bed reactor (10) after regeneration of the first pre-bed reactor (10); a third pathway of olefin metathesis is then started using the first pre-bed reactor again (10). The time on stream in the third pathway using the first pre-bed reactor again is about 30 hours.

Example 1: Standard Process with One Reactor, State of the Art

Catalytic tests were performed in a tubular (4 mm i.d.) continuous-flow fixed-bed reactor made of quartz at 1.4 bar and 300° C. using a $C_2H_4$:trans-2-$C_4H_8$:$N_2$=64.3:25.7:10 feed. $C_2H_4$ (Linde, purity>99.95%), trans-2-$C_4H_8$ (Linde, purity>99.0%) were extra purified with molsieve 3A, while "oxysorb" (Resteck) and molsieve 3A were applied for purifying $N_2$ (Air Liquide, purity>99.999%).

The main catalyst is a physical mixture of MgO (0.3-0.7 mm) and WO$_x$/SiO$_2$ (0.3-0.7 mm) with a weight ratio of 3.0. The MgO (0.3-0.7 mm) was additionally used as a pre-bed arranged upstream. Both beds were placed within the isothermal zone of the reactor. The weight hourly space velocity (WHSV) was of 1.9 h$^{-1}$ related to trans-2-$C_4H_8$ and the main catalyst.

Before catalytic testing, the following pre-treatment was performed. The reactor was heated in a flow of pure nitrogen up to 400° C. with a heating rate of 5 K·min$^{-1}$. The temperature was held constant for 2 h. Hereafter, an air flow was fed to the reactor followed by temperature rising to 525° C. with a heating rate of 5 K·min$^{-1}$. After 2 hours in this flow at the final temperature, the reactor was cooled to 400° C. (2 K·min$^{-1}$) in a flow of pure nitrogen. The temperature was held constant for 0.5 h followed by feeding an $H_2$:$N_2$=30:70 (mol/mol) gas mixture for 0.5 h. Then, the reactor was flushed with a flow of pure nitrogen and heated in the same flow up to 550° C. with a heating rate of 5 K·min$^{-1}$. The temperature was held constant for 16 h. Finally, the reactor was cooled down to 300° C., where the metathesis reaction was studied.

Figure 2:
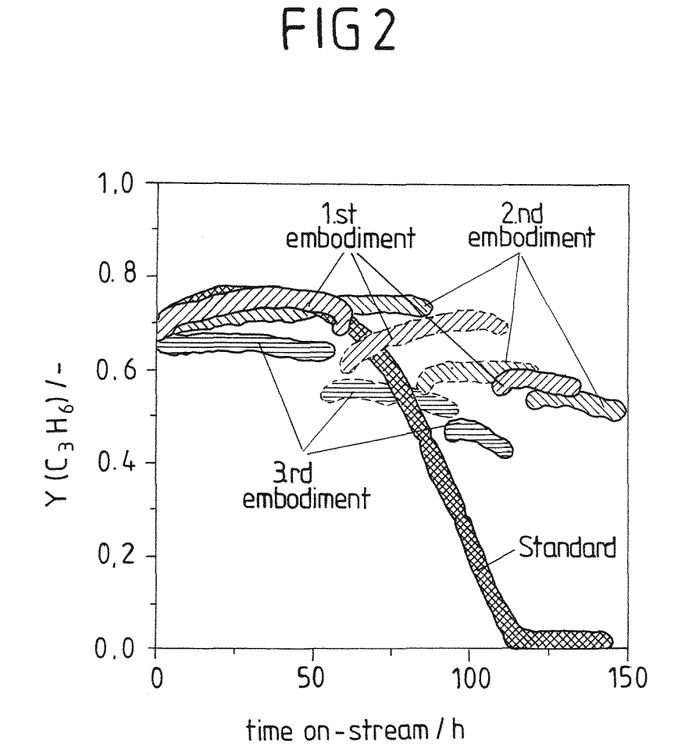
FIG. 2 a Diagram showing the propene yield vs. time on stream for a prior art process and the present process.

The diagram of FIG. 2 shows the yield of propene (equation 3) obtained when the standard catalyst bed configuration (standard curve) is compared with a setup as proposed in this invention disclosure.

Example 2: First Embodiment According to the Invention

The test was carried out under reaction conditions and catalyst bed pre-treatment as described in Example 1 but using 3 separated reactors: 2 for MgO pre-bed and 1 reactor for the main bed, consisting of MgO:(WO$_x$/SiO$_2$)=3:1. The ratio of MgO pre-bed to the main bed was 0.21 (150 mg MgO, 716 mg main catalyst bed).

The results are summarized in the diagram of FIG. 2. The open and solid symbols in this plot distinguish between operation with 1$^{st}$ and 2$^{nd}$ MgO pre-beds without interrupting the flow through the main reactor. The reaction was initially run with the 1$^{st}$ MgO pre-bed until observing the beginning of decrease in propene yield (about 60 h on stream).

Then, the reaction feed was redirected from this pre-bed to the fresh 2$^{nd}$ MgO pre-bed without interrupting the flow through the main reactor. After approximately further 60 hours on stream and diminishing value of propylene yield, the freshly regenerated MgO pre-bed in the first reactor was again used and the metathesis reaction continued using the main catalyst bed without regeneration.

Example 3: Second Embodiment According to the Invention

The test was carried out as described in Example 2 but using ratio of MgO pre-bed to main catalyst bed MgO:(WO$_x$/SiO$_2$) of 0.42 (300 mg pre-bed, 716 mg main catalyst bed). The propene yield with time on stream is shown in FIG. 2.

Example 4: Third Embodiment According to the Invention

The test was carried out as described in Example 2 but using ratio of MgO pre-bed to main catalyst bed MgO:(WO$_x$/SiO$_2$) of 0.84 (600 mg pre-bed, 716 mg main catalyst bed). The propene yield with time on stream is shown in FIG. 2.

The conversion of t-2-$C_4H_8$ was calculated on the basis of inlet and outlet mole fractions (equation 1). The product selectivity was calculated on a molar basis (equation 2). 1-$C_4H_8$ and cis-2-$C_4H_8$ were considered as reaction products. The propene yield is a product of the propylene selectivity and the t-2-butene conversion (equation 3).

$$X_{t-2C_4H_8} = \left(1 - \frac{x_{t-2C_4H_8}^{outlet}}{x_{t-2C_4H_8}^{inlet}}\right) \times 100\% \quad (1)$$

where x is mole fraction of t-2-butene.

$$S_{C_3H_6} = \frac{n^{outlet}_{C_3H_6}}{n^{outlet}_{C_3H_6} + n^{outlet}_{1-C_4H_8} + n^{outlet}_{cis-2C_4H_8} + \sum n^{outlet}_{C_5} + \sum n^{outlet}_{C_6}} \times 100\%, \quad (2)$$

where $n_i^{outlet}$ is number of moles of propene, 1-butene, cis-2-butene, pentenes ($C_5$) and hexenes ($C_6$) at the reactor outlet.

$$Y_{C_3H_6} = S_{C_3H_6} \times X_{t-2-C_4H_8} \times 100\% \quad (3),$$

where $S_{C_3H_6}$ is propene selectivity and $X_{t-2-C_4H_8}$ is conversion of t-2-butene calculated according to equations 1 and 2, respectively.

The examples clearly demonstrate that the time on stream performance for the new 3-reactor process according to the invention in the conversion range of technical interest between two regeneration cycles is extended.

The invention claimed is:

1. A process for obtaining propene from at least two olefins as starting materials by metathesis, wherein one olefin is ethene and the other olefin is n-butene, comprising at least two reaction pathways, wherein
in at least one first reaction pathway at least one stream comprising ethene and n-butene as starting material is fed to at least one first pre-bed reactor with at least one pre-bed comprising magnesium oxide effecting isomerisation of n-butene, and
the stream leaving the at least one first pre-bed reactor is subsequently fed to at least one main catalyst bed reactor downstream of the at least one first pre-bed reactor comprising at least one main catalyst bed comprising at least one first catalyst component comprising tungsten oxide supported on silica, and at least one second catalyst component comprising magnesium oxide, whereby the first and second catalyst are physically mixed with each other,
wherein
in at least one second reaction pathway the at least one stream comprising ethene and n-butene as starting material is re-directed from the at least one first pre-bed reactor to at least one second pre-bed reactor with at least one pre-bed comprising magnesium oxide effecting the isomerisation of the olefin, and
the stream leaving the at least one second pre-bed reactor is subsequently fed to the at least one main catalyst bed reactor downstream of the at least one second pre-bed reactor,
wherein an operational temperature of the first pre-bed reactor and an operational temperature of the second pre-bed reactor are in a range between 150° C. and 350° C. and are lower than an operational temperature of the main catalyst bed reactor, and
wherein the mass ratio of the pre-bed in the first pre-bed reactor and the second pre-bed reactor to the main catalyst bed in the main catalyst bed reactor is between 1:5 and 1:2.

2. The process according to claim 1, wherein the at least one first pre-bed reactor is turned off during the second reaction pathway and is subjected to at least one regeneration cycle during turn-off.

3. The process according to claim 1, wherein the number of reaction pathways is more than two.

4. The process according to claim 1, wherein the time on stream for one reaction pathway is larger than 40 h.

5. The process according to claim 1, wherein the mass ratio of the pre-bed in the first pre-bed reactor and the second pre-bed reactor to the main catalyst bed in the main catalyst bed reactor is between 1:5 and 2.5:1.

6. The process according to claim 1, wherein the operational temperature of the first pre-bed reactor and the operational temperature of the second pre-bed reactor are in a range of 150° C. to 300° C., and the operational temperature of the main catalyst bed reactor is in a range between 250° C. and 350° C.

7. The process according to claim 1, wherein the operational temperature of the first pre-bed reactor and the operational temperature of the second pre-bed reactor are at least 20° C. lower than the operational temperature of the main catalyst bed reactor.

8. The process according to claim 1, wherein the regeneration cycle of the pre-bed of the first pre-bed reactor and the second pre-bed reactor comprises in each case a thermal treatment in an oxygen gas atmosphere at temperatures between 400° C. and 600° C.

9. The process according to claim 1, wherein the main catalyst bed comprises magnesium oxide and tungsten oxide in a mass ratio of between 5:1 and 1:1.

10. The process according to claim 1, wherein the at least one main catalyst bed further comprises oxides of metals of the 6th and 7th group of the PSE deposited on at least one inorganic carrier.

11. The process according to claim 1, wherein the at least one main catalyst bed further comprises Group 2 metal oxides.

12. The process according to claim 1, wherein the pre-bed further comprises an oxide selected from the group consisting of calcium oxide, strontium oxide, barium oxide or mixtures thereof.

13. The process according to claim 4, wherein the time on stream for one reaction pathway is larger than 60 h.

14. The process according to claim 5, wherein the mass ratio of the pre-bed in the first pre-bed reactor and the second pre-bed to the main catalyst bed reactor is between 1:3 and 1:2.

15. The process according to claim 11, wherein the second catalyst component further comprises calcium oxide, barium oxide, strontium oxide, or mixtures thereof.

* * * * *